US009395388B2

(12) United States Patent
Wu et al.

(10) Patent No.: US 9,395,388 B2
(45) Date of Patent: Jul. 19, 2016

(54) METHODS, SYSTEMS, AND COMPUTER READABLE MEDIA FOR DUAL RESONANCE FREQUENCY ENHANCED ELECTROSTATIC FORCE MICROSCOPY

(71) Applicant: The University of North Carolina at Chapel Hill, Chapel Hill, NC (US)

(72) Inventors: Dong Wu, San Leandro, CA (US); Dorothy Erie, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/428,510

(22) PCT Filed: Sep. 16, 2013

(86) PCT No.: PCT/US2013/059965
§ 371 (c)(1),
(2) Date: Mar. 16, 2015

(87) PCT Pub. No.: WO2014/043632
PCT Pub. Date: Mar. 20, 2014

(65) Prior Publication Data
US 2015/0241470 A1    Aug. 27, 2015

Related U.S. Application Data

(60) Provisional application No. 61/701,341, filed on Sep. 14, 2012.

(51) Int. Cl.
*G01Q 60/02* (2010.01)
*B82Y 35/00* (2011.01)
(Continued)

(52) U.S. Cl.
CPC ............... *G01Q 60/02* (2013.01); *G01N 19/00* (2013.01); *G01N 27/60* (2013.01); *G01Q 60/30* (2013.01); *G01Q 60/32* (2013.01); *G01Q 60/36* (2013.01); *G01Q 60/40* (2013.01)

(58) Field of Classification Search
CPC ....... G01N 19/00; G01N 27/60; G01Q 60/02; G01Q 60/24; G01Q 60/32–60/40; G01Q 70/00; G01Q 70/08; G01Q 70/14; G01Q 70/16; B82Y 35/00
USPC ................. 850/22, 29, 33, 37–41, 56, 59, 60; 73/105

See application file for complete search history.

(56) References Cited

U.S. PATENT DOCUMENTS 5,003,815 A    4/1991    Martin et al.
5,261,015 A    11/1993    Glasheen
(Continued)

OTHER PUBLICATIONS

Cleveland et al, "Energy Dissipation in Tapping-Mode Atomic Force Microscopy", Applied Physics Letters, vol. 72 No. 20, 1998.*
(Continued)

*Primary Examiner* — Jack Berman
*Assistant Examiner* — David E Smith
(74) *Attorney, Agent, or Firm* — Jenkins, Wilson, Taylor & Hunt, P.A.

(57) ABSTRACT

The subject matter described herein includes methods, systems, and computer readable media for dual resonance frequency enhanced electrostatic force microscopy. One method includes applying an alternating current (AC) bias and a direct current (DC) bias to an atomic force microscopy cantilever, wherein the AC bias has a frequency greater than a fundamental resonance frequency of the cantilever. The method further includes mechanically vibrating the cantilever at a frequency different from the frequency of the AC bias. The method further includes physically and electrostatically scanning a sample in the same pass using the cantilever while vibrating the cantilever and applying the AC and DC biases to the cantilever, and generating a topology image of the sample from the physical scanning and an electrostatic image of charged material under or on a surface of the sample from the electrostatic scanning.

30 Claims, 4 Drawing Sheets

(51) Int. Cl.
*G01Q 60/30* (2010.01)
*G01N 19/00* (2006.01)
*G01N 27/60* (2006.01)
*G01Q 60/32* (2010.01)
*G01Q 60/36* (2010.01)
*G01Q 60/40* (2010.01)

(56) References Cited

U.S. PATENT DOCUMENTS

| | | | |
|---|---|---|---|
| 5,357,105 A | 10/1994 | Harp et al. | |
| 5,440,121 A | 8/1995 | Yasutake et al. | |
| 5,445,011 A | 8/1995 | Ghislain et al. | |
| 5,513,518 A | 5/1996 | Lindsay | |
| 5,515,719 A | 5/1996 | Lindsay | |
| 5,581,082 A | 12/1996 | Hansma et al. | |
| 5,595,942 A | 1/1997 | Albrecht et al. | |
| 5,612,491 A | 3/1997 | Lindsay | |
| 5,670,712 A | 9/1997 | Cleveland et al. | |
| 5,737,086 A | 4/1998 | Gerber et al. | |
| 5,750,989 A | 5/1998 | Lindsay et al. | |
| 5,753,814 A | 5/1998 | Han et al. | |
| 5,854,487 A * | 12/1998 | Braunstein et al. | 850/9 |
| 5,929,440 A | 7/1999 | Fisher | |
| 6,073,485 A * | 6/2000 | Kitamura | B82Y 35/00 73/105 |
| 6,080,988 A | 6/2000 | Ishizuya et al. | |
| 6,118,124 A | 9/2000 | Thundat et al. | |
| 6,185,991 B1 | 2/2001 | Hong et al. | |
| 6,330,824 B1 | 12/2001 | Erie et al. | |
| 6,337,478 B1 * | 1/2002 | Uehara | B82Y 35/00 250/216 |
| 6,507,197 B1 | 1/2003 | Itoh et al. | |
| 2006/0225164 A1 * | 10/2006 | Williams et al. | 977/852 |
| 2009/0307809 A1 * | 12/2009 | Ziegler | B82Y 35/00 850/62 |
| 2010/0201586 A1 | 8/2010 | Michalk | |
| 2013/0085714 A1 * | 4/2013 | Itoh | G01Q 60/30 702/150 |

OTHER PUBLICATIONS

Rache et al, "Van der Waals Forces", Chemwiki, http://chemwiki.ucdavis.edu/Physical_Chemistry/Physical_Properties_of_Matter/Atomic_and_Molecular_Properties/Intermolecular_Forces/Van_der_Waals_forces.*
Digital Instruments, Support Note 230, Rev. A, "Electric Force Microscopy", 1996.*
Mikamo-Satoh, et al. "Electrostatic Force Microscopy: Imaging DNA and Protein Polarizations One by One", Nanotechnology 20 (2009) 145102.*
Stark et al, "Multifrequency Electrostatic Force Microscopy in the Repulsive Regime", Nanotechnology 18 (2006) 065502.*
Notification of Transmittal of the International Search Report and the Written Opinion of the International Searching Authority, or the Declaration for International Application No. PCT/US2013/059965 (Dec. 9, 2013).
Albrecht et al., "Frequency modulation detection using high-Q cantilevers for enhanced force microscope sensitivity," Journal of Applied Physics, vol. 69, No. 2, pp. 668-673 (1991).
Barnes et al., "Erratum: A femtojoule calorimeter using micromechanical sensors," Review of Scientific Instruments, vol. 65, No. 12, pp. 3793-3798 (Dec. 1994).
Barth et al., "Recent Trends in Surface Characterization and Chemistry with High-Resolution Scanning Force Methods," Advanced Materials, vol. 23, pp. 477-501 (2011).
Bazett-Jones et al. "Visualization and analysis of unfolded nucleosomes associated with transcribing chromatin," Nucleic Acids Research, vol. 24, No. 2, pp. 321-329 (1996).
Colchero et al., "Resolution enhancement and improved data interpretation in electrostatic force microscopy," Physical Review B, vol. 64, Issue 24 (2001).

Ding et al., "Improving lateral resolution of electrostatic force microscopy by multifrequency method under ambient conditions," Applied Physics Letters, vol. 94 (2009).
García et al., "Dynamic atomic force microscopy methods," Surface Science Reports, vol. 47, pp. 197-301 (2002).
Giessibl, "Atomic Resolution of the Silicon (111)-(7×7) Surface by Atomic Force Microscopy," Science, vol. 267, pp. 68-71 (Jan. 6, 1995).
Gil et al., "Electrostatic force gradient signal: resolution enhancement in electrostatic force microscopy and improved Kelvin probe microscopy," Nanotechnology, vol. 14, pp. 332-340 (2003).
Gimzewski et al., "Observation of a chemical reaction using a micromechanical sensor," Chemical Physics Letters, vol. 217, No. 5,6, pp. 589-594 (Jan. 28, 1994).
Glatzel et al., "Amplitude or frequency modulation-detection in Kelvin probe force microscopy," Applied Surface Science, vol. 210, pp. 84-89 (2003).
Han et al., "A magnetically driven oscillating probe microscope for operation in liquids," Applied Physics Letters, vol. 69, No. 26, pp. 4111-4113 (Dec. 23, 1996).
Hansma et al., "Tapping mode atomic force microscopy in liquids," Applied Physics Letters, vol. 64, No. 13, pp. 1738-1740 (Mar. 28, 1994).
Hillier et al., "ac-mode atomic force microscope imaging in air and solution with a thermally driven bimetallic cantilever probe," Review of Scientific Instruments, vol. 68, No. 5, pp. 2082-3090 (May 1997).
Hong et al., "Detection and control of ferroelectric domains by an electrostatic force microscope," Journal of Vacuum Science & Technology B, vol. 16, No. 6, pp. 2942-2946 (1998).
Hong et al., "Measurement of hardness, surface potential, and charge distribution with dynamic contact mode electrostatic force microscope," Review of Scientific Instruments, vol. 70, No. 3, pp. 1735-1739 (Mar. 1999).
Hoummady et al., "Enhanced sensitivity to force gradients by using higher flexural modes of the atomic force microscope cantilever," Applied Physics A, vol. 66, Issue S1, pp. 361-364 (1998).
Hu et al., "Scanning polarization force microscopy: A technique for imaging liquids and weakly adsorbed layers," Applied Physics Letters, vol. 67, No. 4, pp. 476-478 (Jul. 24, 1995).
Jiang et al., "Atomic force microscopy captures MutS tetramers initiating DNA mismatch repair," The European Molecular Biology Organization Journal, vol. 30, No. 14, pp. 2881-2893 (2011).
Kunkel et al., "DNA Mismatch Repair," Annual Review of Biochemistry, vol. 74, pp. 681-710 (2005).
Lee et al., "Development of a piezoelectric self-excitation and self-detection mechanism in PZT microcantilevers for dynamic scanning force microscopy in liquid," J. Vac. Sci. Technol. B, vol. 15, No. 4, pp. 1559-1563 (Jul./Aug. 1997).
Leung et al., "Improved Kelvin probe force microscopy for imaging individual DNA molecules on insulating surfaces," Applied Physics Letters, vol. 97, pp. 203703-1-203703-3 (2010).
Leung et al., "Imaging Surface Charges of Individual Biomolecules," Nano Letters, vol. 9, No. 7, pp. 2769-2773 (2009).
Lyubchenko et al., "Atomic Force Microscopy of DNA, Nucleoproteins and Cellular Complexes: The Use of Functionalized Substrates," Scanning Microscopy Supplement, vol. 10, pp. 97-109 (1996).
Martin et al., "Atomic force microscope-force mapping and profiling on a sub-100-Å scale," Journal of Applied Physics, vol. 61, No. 10, pp. 4723-4729 (May 15, 1987).
Naito et al., "Electrostatic force at mica surfaces proved by frequency-shift spectroscopy," Surface Science, vol. 459, pp. L446-L450 (2000).
Nonnenmacher et al., "Kelvin probe force microscopy", Applied Physics Letters, vol. 58, No. 25, pp. 2921-2923 (Jun. 24, 1991).
Putman et al., "Tapping mode atomic force microscopy in liquid," Applied Physics Letters, vol. 64, No. 18, pp. 2454-2456 (May 2, 1994).
Rast et al., "The noise of cantilevers," Nanotechnology, vol. 11, pp. 169-172 (2000).

(56) References Cited

OTHER PUBLICATIONS

Ratcliff et al., "A Novel Single-Molecule Study to Determine Protein-Protein Association Constants," Journal of the American Chemical Society, vol. 123, pp. 5632-5635 (2001).

Ratcliff et al., "Photothermal Modulation for Oscillating Mode Atomic Force Microscopy in Solution," Applied Physics Letters, vol. 72, No. 15, pp. 1911-1913 (Apr. 13, 1998).

Shlyakhtenko et al,. "Silatrane-based surface chemistry for immobilization of DNA, protein-DNA complexes and other biological materials," Ultramicroscopy, vol. 97, pp. 279-287 (2003).

Sokolov et al., "Improved atomic force microscopy resolution using an electric double layer," Applied Physics Letters, vol. 70, No. 7, pp. 844-846 (Feb. 17, 1997).

Takagi et al., "Electrostatic force spectroscopy on insulating surfaces: the effect of capacitive interaction," Nanotechnology, vol. 20, pp. 1-7 (Aug. 19, 2009).

Tevaarwerk et al., "Quantitative analysis of electric force microscopy: The role of sample geometry," Review of Scientific Instruments, vol. 76, pp. 053707-1-053707-5 (2005).

Umeda et al., "Scanning attractive force microscope using photothermal vibration," Journal of Vacuum Science & Technology B, vol. 9, No. 2, pp. 1318-1322 (Mar./Apr. 1991).

Varesi et al., "Photothermal measurements at picowatt resolution using uncooled micro-optomechanical sensors," Applied Physics Letters, vol. 71, No. 3, pp. 306-308 (Jul. 21, 1997).

Wang et al., "DNA bending and unbending by MutS govern mismatch recognition and specificity," Proceedings of the National Academy of Sciences of the USA, vol. 100, No. 25, pp. 14822-14827 (Dec. 9, 2003).

Yang et al., "Quantitative characterization of biomolecular assemblies and interactions using atomic force microscopy," Methods, vol. 29, Issue 2, pp. 175-187 (2003).

\* cited by examiner

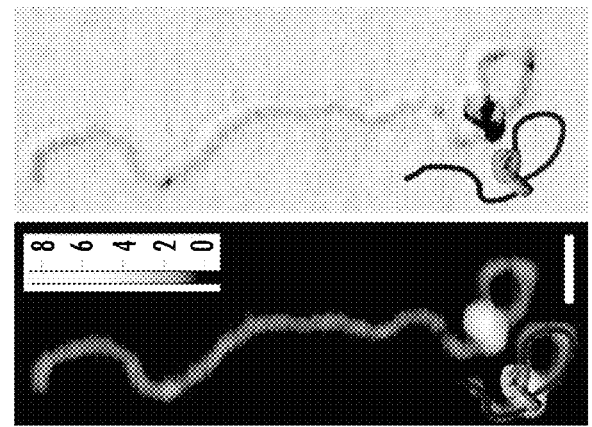
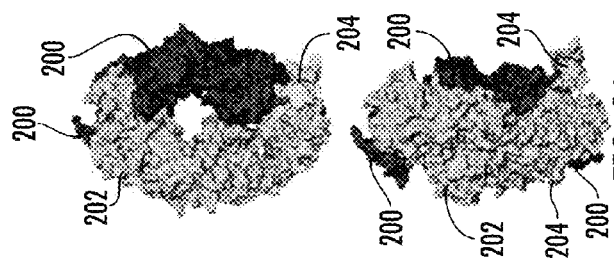
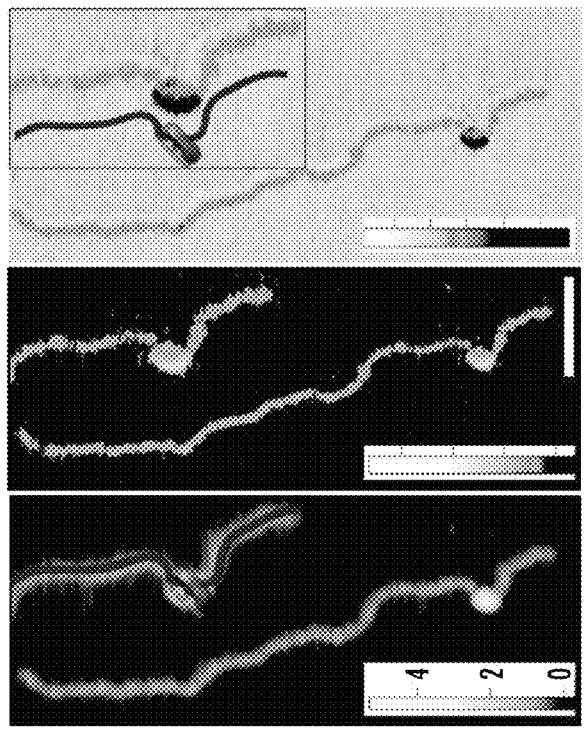
FIG. 2A
FIG. 2B
FIG. 2C
FIG. 2D

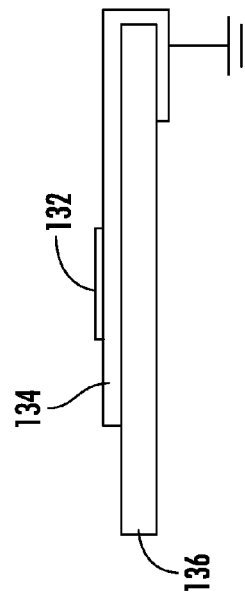
FIG. 3A
FIG. 3B
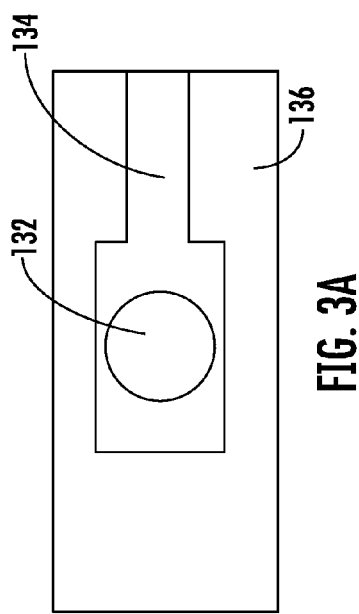
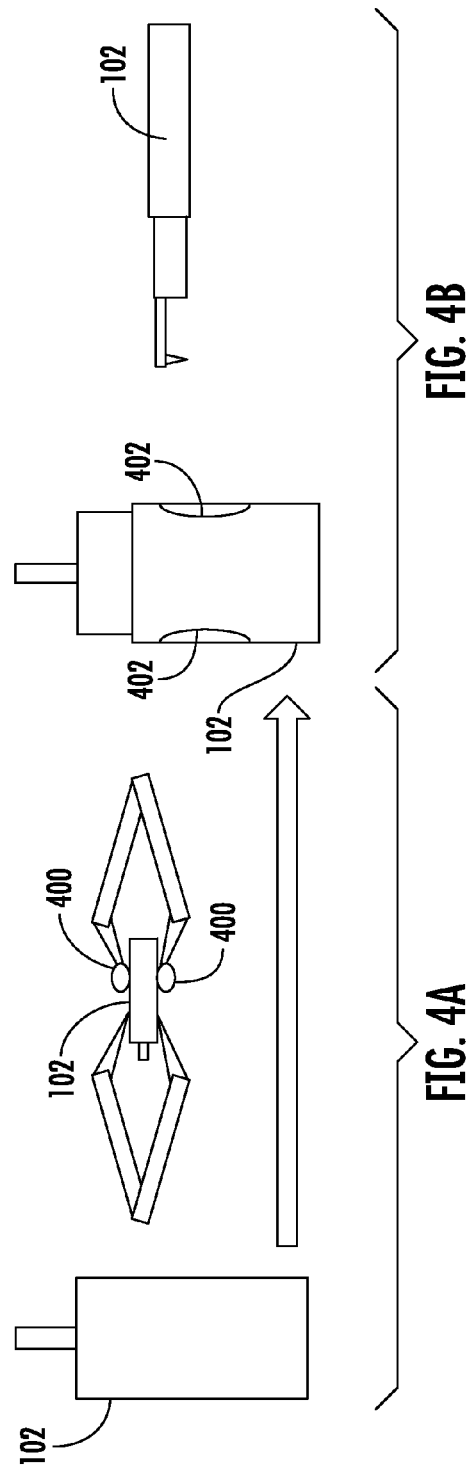
FIG. 4A
FIG. 4B

METHODS, SYSTEMS, AND COMPUTER READABLE MEDIA FOR DUAL RESONANCE FREQUENCY ENHANCED ELECTROSTATIC FORCE MICROSCOPY

PRIORITY CLAIM

This application claims the benefit of U.S. Provisional Patent Application Ser. No. 61/701,341, filed Sep. 14, 2012; the disclosure of which is incorporated herein by reference in its entirety.

GOVERNMENT INTEREST

This invention was made with government support under Grant No. R01 GM079480 (DAE) awarded by the National Institutes of Health. The government has certain rights in the invention.

TECHNICAL FIELD

The subject matter described herein relates to mechanically scanning and electrostatically imaging biological samples. More particularly, the subject matter described herein relates to methods, systems, and computer readable media for dual resonance frequency enhanced electrostatic force microscopy.

BACKGROUND

Single-molecule, high-resolution imaging of protein-nucleic acid complexes using techniques such as electron microscopy (EM) and atomic force microscopy (AFM) provides invaluable information about the structure-function relationships of biological processes. A significant limitation to these techniques, however, is the inability to resolve the location of the nucleic acid within protein complexes. Electron spectroscopic imaging selecting for phosphorous coupled with image averaging has been used to characterize the DNA content of nucleosomes[1]; however, there are no methods that allow visualization of DNA within protein-DNA complexes at a single molecule level. Because both proteins and DNA are significantly charged and interactions between proteins and DNA result in charge neutralization, we reasoned that it may be possible to visualize the path of DNA inside protein-DNA complexes by high-resolution imaging of their electrostatic potential.

Electrostatic force microscopy (EFM) and Kelvin probe force microscopy (KPFM) have been used to image the electrostatic surface potential of a large variety of materials with high spatial resolution and sensitivity[2]. There are several different modes of EFM and KPFM. Generally, a modulated bias voltage ($V_{DC}+V_{AC}\sin(\omega t)$) is applied between the tip and sample. This bias generates an electrostatic force between the tip and the sample, which is the sum of three components[3,4]:

$$F_{DC} = \frac{1}{2}\frac{\partial C}{\partial z}\left[(\Delta\phi_{TS} - V_{DC})^2 + \frac{V_{AC}^2}{2}\right] \quad (1)$$

$$F_\omega = -\frac{\partial C}{\partial z}[(\Delta\phi_{TS} - V_{DC})V_{AC}\sin(\omega t)] \quad (2)$$

$$F_{2\omega} = \frac{1}{4}\frac{\partial C}{\partial z}[V_{AC}^2\cos(2\omega t)] \quad (3)$$

where $\Delta\phi_{TS}$ and $\partial C/\partial z$ are the contact potential difference and capacitance gradient, respectively, between the tip and the sample. This force induces a vibration in the cantilever at the frequency of the AC bias ($\omega$). In KPFM, a feedback loop is used to adjust $V_{DC}$ such that it compensates for $\Delta\phi_{TS}$, thereby nullifying $F_\omega$ and generating a potential map of the surface; whereas, in EFM, there is no feedback voltage, and images are produced by monitoring the amplitude (and phase) of the vibration. Dual-frequency single-pass techniques, where the topography and the surface electrical potential are captured simultaneously have the highest sensitivity[2,4,5]. In fact, dual-frequency KPFM has been used to obtain images of DNA[5] and transcription complexes[6]; however, no details about the protein-DNA complex were revealed.

Accordingly, there exists a need for improved methods, systems, and computer readable media for imaging a biological sample, including charged structures residing beneath the surface of the sample.

SUMMARY

The subject matter described herein includes methods, systems, and computer readable media for dual resonance frequency enhanced electrostatic force microscopy. One method includes applying an alternating current (AC) bias and a direct current (DC) bias to an atomic force microscopy cantilever, wherein the AC bias has a frequency greater than a fundamental resonance frequency of the cantilever. The method further includes mechanically vibrating the cantilever at a frequency different from the frequency of the AC bias. The method further includes physically and electrostatically scanning a sample in the same pass using the cantilever while vibrating the cantilever and applying the AC and DC biases to the cantilever, and generating a topology image of the sample from the physical scanning and an electrostatic image of charged material under or on a surface of the sample from the electrostatic scanning.

The subject matter described herein may be implemented in hardware, software, firmware, or any combination thereof. As such, the terms "function" "node" or "module" as used herein refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which:

FIGS. 2a-2d are images of biological samples produced by the system illustrated in FIG. 1a;

FIGS. 3a and 3b illustrate sample substrate preparation according to an embodiment of the subject matter described herein;

FIGS. 4a and 4b illustrate cantilever preparation according to an embodiment of the subject matter described herein.

DETAILED DESCRIPTION

Figures 1A, 1B:
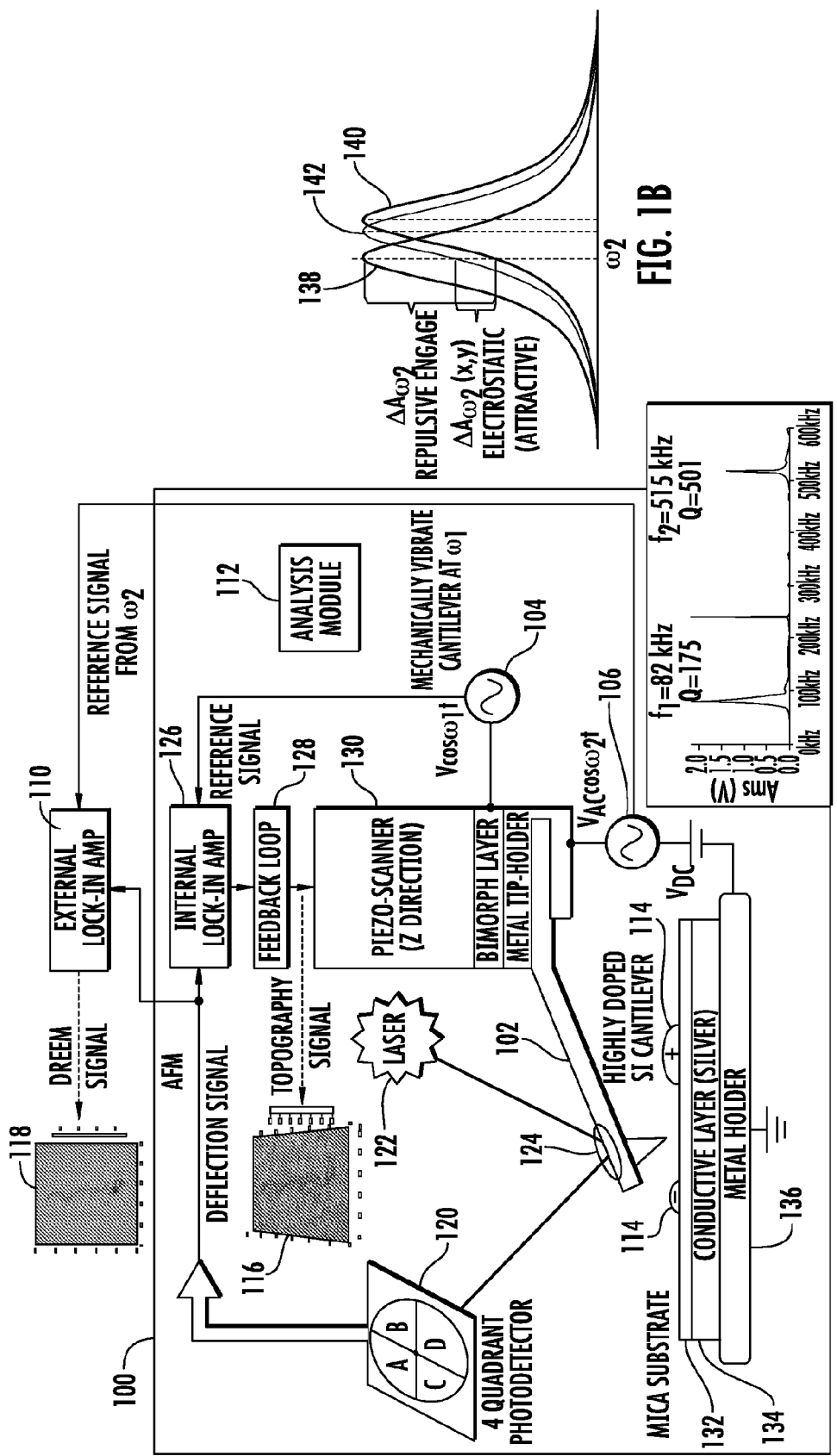
FIG. 1a is a block diagram illustrating a system for dual resonance frequency enhanced electrostatic force microscopy according to an embodiment of the subject matter described herein.
FIG. 1b is a graph illustrating the frequency of signals applied to cantilever 102 according to an embodiment of the subject matter described herein.

Considering the weak electrostatic signals generated by DNA and proteins, we developed a sensitive high-resolution Dual-Resonance-frequency Enhanced EFM (DREEM) to resolve the DNA within protein-DNA complexes deposited on mica (FIG. 1a and Methods). We adapted and extended the dual frequency single-pass techniques that take advantage of the resonance properties of the cantilever[4,5,7]. To maximize resolution in both the topographic and DREEM images, we use sharp highly doped silicon cantilevers and operate in repulsive intermittent contact mode (Methods). Operating in repulsive mode keeps the tip at a constant minimal distance from the sample, which in turn, maximizes the sensitivity of detection of the electrostatic potential. To simultaneously obtain topographic and DREEM images, we monitor the surface potential by applying a modulated bias voltage to the tip at the first overtone ($\omega_2$), while simultaneously using standard repulsive intermittent contact mode topographic imaging near the fundamental resonance ($\omega_1$) (FIG. 1a)[7]. Using the first overtone for electrostatic imaging and the fundamental frequency for topographic imaging has several advantages. First, it is preferable to conduct topographic imaging of soft samples with a minimal force to avoid damage, and the effective force constant at $\omega_1$ is forty times less than that at $\omega_2$ [$k_2=k_1(\omega_2/\omega_1)^2$]. Second, the Q-factor of the peak at $\omega_2$ is higher than that of $w_1$ (~500 vs ~170), thus $\omega_2$ is more sensitive to changes in force gradient than $\omega_1$[8]. Third, the contribution of the cantilever to the electrostatic force is minimized at $\omega_2$, thereby enhancing spatial resolution in the DREEM image[9].

Instead of using the DC bias to nullify $F_\omega$ as is done in KPFM, we take advantage of the negative charge of mica[6] and use the DC bias together with the AC bias to generate a vibration at $\omega_2$. We then monitor the change in vibration amplitude ($A_{\omega 2}$) and phase as a function of sample position. We obtained the highest resolution DREEM amplitude and phase images with $V_{DC}$=−0.3 to −0.5 V and $V_{AC}$=16 to 20 V (Methods). Operating in repulsive mode using these voltages, $A_{\omega 2}$~1 nm, which is ~50 times smaller than the mechanical vibration amplitude ($A_{\omega 1}$) at the fundamental frequency. This $A_{\omega 2}$ is sufficiently large to produce high quality DREEM images and yet small enough compared to $A_{\omega 1}$ that no crosstalk between the DREEM and topographic signals is observed. $A_{\omega 2}$ depends on the force gradient, $\partial F/\partial z$ (F'), as well as the force, at $\omega_2$, because F' changes the effective spring constant of the cantilever and shifts its resonance frequency, which in turn, reduces $A_{\omega 2}$ (FIG. 1b)[10]. Upon engaging in repulsive mode, the force gradient due to repulsive atomic interactions (F'$\omega_2$, a) causes the resonance peak to shift to a higher frequency, significantly reducing $A_{\omega 2}$ (FIG. 1b). During scanning, F'$\omega_2$, a is kept constant via the topographic signal at $\omega_1$, and therefore, changes in $A\omega_2$ [$\Delta A_{\omega 2}$(x, y)] depend primarily on the electrostatic force and force gradient. For small changes in electrostatic potential, the frequency shift due to changes in force gradient will dominate $\Delta A_{\omega 2}$(x,y), with the electrostatic force making only a small contribution (FIG. 1b and Methods)[11]. The DREEM amplitude signal reports on the strength of the electrostatic force gradient, including the static force gradient (F'$_{DC}$) (Methods). The DREEM phase is related to the energy dissipation[12] and, therefore, has a complex dependence on the potential and other properties of the sample. Notably, monitoring F' instead of $F_\omega$ significantly increases spatial resolution and sensitivity, because F' has a shorter distance dependence than $F_\omega$[11,13] and a quadratic dependence on the change in electrostatic potential (Methods). The spatial resolution of the DREEM images, like that of the topographic images, appears to be limited by the tip size.

We demonstrate the capabilities of DREEM by imaging complexes of mismatch repair (MMR) proteins bound to DNA. In MMR, MutS homologs recognize mismatches and subsequently form multimeric complexes with MutL homologs in the presence of ATP[14]. MutS is a dimer with DNA binding and ATPase domains, and the DNA binding domains encircle and bend the DNA (FIG. 2a)[15]. In addition, two MutS dimers can associate to form loops[16,17]. AFM images (FIG. 2b,c) of T. aquaticus (Taq) MutS bound to a GT mismatch and two MutS dimers forming a loop between the mismatch and a DNA end show the typical smooth peaks on the DNA corresponding to Taq MutS[16]. In the DREEM images, the protein and the DNA show an increase in amplitude and a decrease in phase, respectively, relative to the mica surface, with the protein producing greater contrast, consistent with previous studies[5,6]. Notably; however, the path of the DNA through MutS, which is hidden in the AFM image, can be seen in DREEM images, because the interaction of the DNA with protein changes the distribution of the local electrical field and reduces the DREEM signal relative to the protein alone. This reduction in potential is expected due to charge neutralization associated with the protein-DNA interaction. Inspection of these and other images (not shown) suggest that the contrast between the DNA and protein depends on how close the protein-DNA interaction site is to the tip. If the DNA is underneath a large amount of protein, then the electrostatic properties of the protein will likely screen out the effect of the DNA. In addition to visualizing the DNA inside the complex, the DREEM data taken together with structural data on MutS[15] allow us to model the general orientation of the MutS dimers in the complexes (FIG. 2b,c). The power of DREEM is truly revealed in the image of a large multiprotein complex of human MutSα and MutLα bound to DNA containing a GT mismatch (FIG. 2d). In the topographic image, a large protein complex is seen on the end of the DNA. The volume of this complex is consistent with it containing ~10 proteins[18]. The length of the DNA that is not inside the protein complex is ~120 nm shorter than the expected length of the DNA. Inspection of the DREEM amplitude and phase images reveals the path of the DNA in this large complex. Including the DNA inside the protein yields a DNA length that is within 5% of the expected length.

In summary, the capability of DREEM to detect very small changes in electrostatic potential with high resolution makes it is powerful tool for characterizing the structure of protein-DNA complexes. It provides unprecedented detail about the conformation of DNA in individual protein-DNA complexes, and it will likely be useful for studying the electrostatic properties of other biological specimens, such as, viruses and membranes, as well as non-biological samples, such as polymers and other materials. Finally, with the addition of a few components (FIG. 1a), DREEM can be readily implemented on many of the commercially available AFMs.

FIG. 1a illustrates an instrumental design for simultaneous AFM and DREEM imaging. In FIG. 1a, an AFM 100 (MFP-3D, Asylum Research) is operated in repulsive oscillating (intermittent contact) mode with a cantilever 102 mechanically vibrated near its resonance frequency by an AC source 104 ($\omega_1=2\pi f_1$) ($\omega_{mec}/2\pi=\sim80$ kHz, for the cantilever used in this study) to collect the topographic information. To simultaneously collect the DREEM image, AC and DC biases are respectively applied by sources 106 and 108 to highly doped silicon cantilever 102 (Nanosensors, PPP-FMR, Force constant 2.8 N/m), with the frequency of the AC bias centered on cantilever's first overtone ($\omega_2=2\pi f_2$) ($\omega_{elec}/2\pi=f_2\sim500$ kHz). Sources 104, 106, and 108 may be implemented by a function generator capable of generating AC signals and applying a DC bias. An external lock-in amplifier 110 is used to separate the $\omega_2$ component from the output signal and compare it with the reference input AC signal to generate the electrostatic amplitude and phase signals. The DC bias is maintained constant and is used to adjust the electrical vibration amplitude to produce optimal contrast in the DREEM images. The choice of DC bias is essential to obtaining high-resolution images and is discussed in Methods. In the current setup, the AC and DC biases can be adjusted from 0 V to 20 V and −0.8 V to 0.8 V, respectively.

An analysis module 112 controls the physical and electrostatic scanning of a sample 114 and the generation of a topography image 116 from the mechanical scanning and an electrostatic image 118 from the electrostatic scanning. The electrostatic image may show charged material under or on the surface of a sample, as illustrated in FIG. 2d.

In order to sense the position of cantilever 102, AFM 100 includes a four quadrant photo detector 120 that detects light from a light source 122 that is reflected from a surface 124 positioned on the end of the cantilever 102. The output of photodetector 120 is provided to an internal lock in amplifier 126 and through a feedback loop 128 to a piezo scanner 130, which controls the motion of cantilever 102 in the z direction.

Sample 114 is mounted on a mica substrate 132. Mica substrate 132 is mounted on a conductive layer 134 which connects mica substrate 132 to ground. Conductive layer 134 may be a silver paced or other suitable material. Mica substrate 132 and conductive layer 134 are mounted on a glass substrate 136. Although not illustrated in FIG. 1A, conductive layer 134 may extend around the periphery of glass substrate 136 to make a suitable ground connection.

FIG. 1b is a diagram showing the principle of DREEM. Upon excitation of the tip with a DC and AC bias at $\omega_2$, the cantilever vibrates at $\omega_2$ due to the surface charge (curve 138). After engaging in repulsive intermittent contact, the first overtone shifts to a higher frequency (curve 140) and the $A\omega_2$ is reduced ($\Delta A_{\omega_2}$ repulsive engage). The attractive electrostatic interaction causes a shift to lower frequencies (curve 142), and $\Delta A_{\omega_2}$ (x,y) is the change in amplitude due to changes in electrostatic interaction.

FIGS. 2a-2d illustrate AFM and DREEM images of mismatch repair complexes. FIG. 2a illustrates a space-filling model of the crystal structure of Taq MutS (generated from PDB 1EWQ). Subunits A and B and the DNA are labeled 200, 202, and 204 respectively. FIG. 2b illustrates AFM (left) and DREEM amplitude (center) and phase (right) images of a Taq MutS-mismatch complex. FIG. 2c illustrates AFM (left) and DREEM phase (right) images of two MutS dimers forming a loop in the DNA between the mismatch and the DNA end. Models of the complexes are shown overlaid on the AFM images and next to the phase images. FIG. 2d illustrates AFM (left) and DREEM phase (middle & right) images of a large MutSα-MutLα-DNA complex containing ~10 proteins. In the AFM image of the complex, the DNA measures ~120 nm too short. The DREEM image reveals that this missing DNA is wrapped in the complex (the path of the DNA is traced in the inset). Interestingly, the DNA appears to be sharply bent after entering the complex at the expected position of the mismatch (MM). White bar represents 100 nm. Z-scale bars are shown for AFM images in units of nanometers. Z-scale bars (with arbitrary units) for the DREEM images are shown in FIG. 2b.

FIGS. 3a and 3b illustrate, respectively, a top view and a side view of a substrate suitable for use with embodiments of the subject matter described herein. As illustrated in FIGS. 3a and 3b, mica substrate 132 is mounted on conductive layer 134, which is mounted on glass slide 136. Conductive layer 134 is then grounded to mica substrate 132 in order to reduce background noise.

FIGS. 4a and 4b illustrate exemplary preparation of cantilever 102 for use with embodiments of the subject matter described herein. In FIG. 4a, tweezers remove the cantilever's surface oxidized layer to make conductive connection with drops of sliver paste 400. FIG. 4b shows the results of cantilever 102 with portions 402 where the oxidized surface layer is removed for conductive connection.

Figure 5:
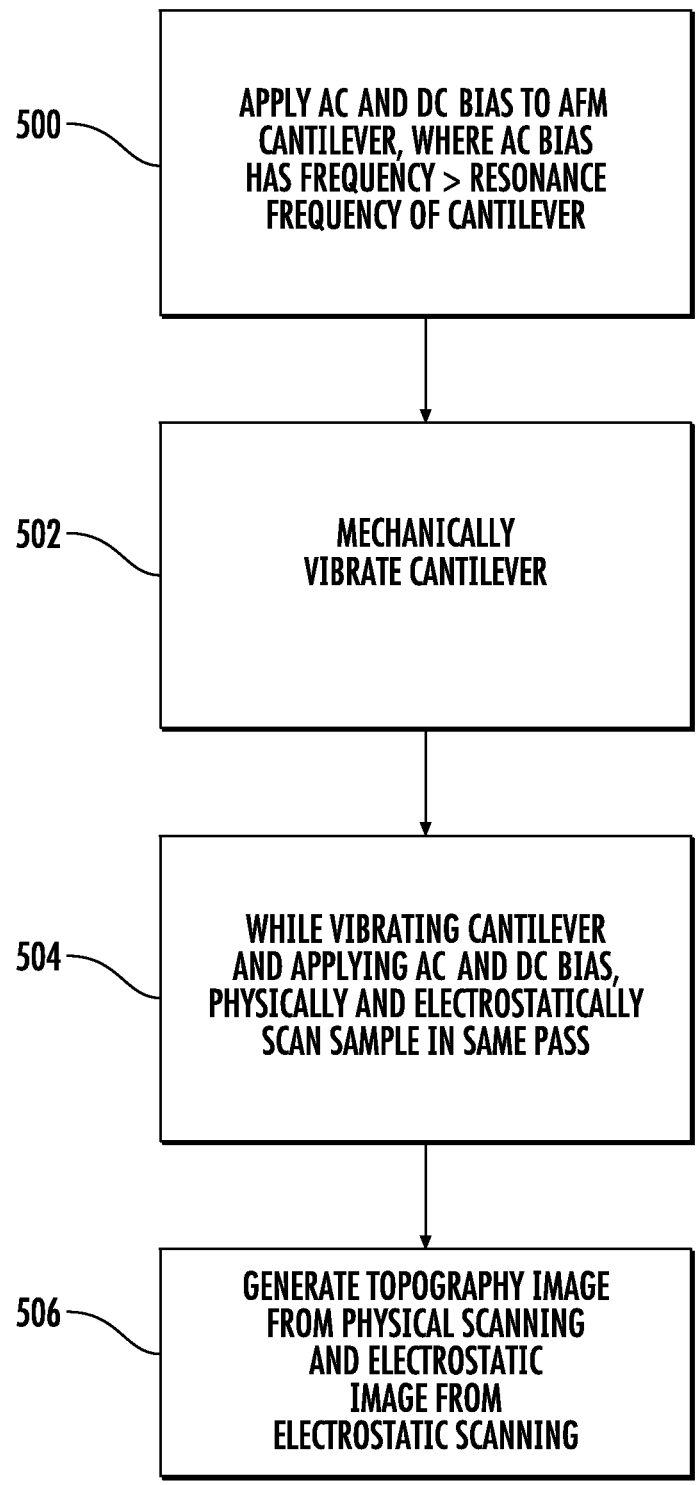
FIG. 5 is a flow chart illustrating an exemplary process for enhanced surface and electrostatic imaging according to an embodiment of the subject matter described herein.

FIG. 5 is a flow chart illustrating exemplary steps for enhanced electrostatic and atomic force microscopy according to an embodiment of the subject matter described herein. Referring to FIG. 5, in step 500, an AC bias and a DC bias are applied to an AFM cantilever. The AC bias has a frequency greater than the fundamental resonance frequency of the cantilever. In one example, the AC bias may be set to a frequency substantially equal to the first overtone frequency of the cantilever. In step 502, the cantilever may be mechanically vibrated at or near the fundamental frequency of the cantilever. The mechanical vibration may be distinct or separate from the AC bias.

In step 504, the sample is physically and electrostatically scanned in the same pass using the cantilever while vibrating and applying the AC and DC biases to the cantilever. In step 506, a topography image of the sample is generated from the physical scanning and an electrostatic image of charged material under or on a surface of the sample is generated from the electrostatic scanning.

Methods
Instrument Design
Our experimental setup for simultaneous AFM and DREEM is described in FIG. 1.
Theoretical Basis of DREEM Measurements:

In our setup, we apply an AC bias at the first overtone and monitor the change in vibration amplitude [$\Delta A_{\omega_2}$ (x,y)] as a function of position. As demonstrated below, because we are monitoring very small changes in surface potential on a modestly charged surface (mica), $\Delta A_{\omega_2}$ (x,y) will be dominated by changes in the force gradient, with only small contributions from the force. This method is similar to amplitude slope detection method used to monitor the atomic force gradient in topographic AFM images[11].

Because the AC bias is applied at the first overtone frequency ($\omega_2$), the applied force induces a vibration, with a free amplitude (no dampening)

$$A_{0,\omega_2}=a(Q_2/k_2)F_{\omega_2}=a(Q_2/k_2)(\Delta\phi_{TS}-V_{DC})V_{AC},$$

where $Q_2$ and $k_2$ are the quality factor and effective spring constant, respectively, of the first overtone of the cantilever, and a is a constant that depends on the capacitance gradient, tip radius and tip-sample separation[3,19,20]. In addition, the force gradient, $\partial F/\partial_z$ (F'), changes the effective spring constant of the cantilever and shifts its resonance frequencies by $$\Delta\omega_2 = \omega_2 F'/2k_c$$

where $k_c$ is the spring constant of the cantilever (which is equal to $k_1$, the spring constant of $\omega_1$)[8,10,11], thereby reducing the vibration amplitude at $\omega_2$ to $$A_{\omega_2} \approx A_{0,\omega_2}[1+b(Q_2/k_c)F']$$

This approximation assumes that the applied force is just off the resonance frequency, where the slope of the peak is maximum and $b=2/3\sqrt{3}$[11]. Notably, the frequency shift depends on both the static and dynamic components of the electrostatic force gradient (i.e., $F'_{DC}$ and $F'_{\omega_2}$) and is dominated by $F'_{DC}$, which depends on $(\Delta\phi_{TS}-V_{DC})^2$[21].

Because we are operating in intermittent contact, the force gradient (F'a) due to repulsive atomic interactions is significantly greater than those due to the attractive electrostatic interactions $(F'_{el})$[22,23], and therefore, $\Delta\omega_2>0$. (We verified that $\Delta\omega_2>0$ in our experiments by monitoring the vibration amplitude as a function of the AC bias frequency (data not shown).) Under our imaging conditions, $A_{\omega_2}$ is $\sim 1/2 A_{0,\omega_2}$ after engaging in repulsive mode. During scanning, however, $F_a'$ should be constant because the topographic signal at $\omega_1$ maintains a constant atomic force gradient, and therefore, changes in $\Delta\omega_2$ (x,y) will be dominated by $F_{el}'$.

Assuming that the atomic force gradient is constant as a function of x,y position of the tip, the change in $A_{\omega_2}$ ($\Delta A_{\omega_2}$(x, y)) due to changes in the electrostatic force and force gradient as a function of position on the surface is approximately $$\Delta A_{\omega_2}(x,y) \approx (aQ_2/k_2)[\Delta F_{\omega_2,el}(x,y)+b(Q_2/k_c)\Delta(F_{\omega_2,el}(x,y)F_{el}'(x,y))]$$

$$\Delta A_{\omega_2}(x,y) \approx (aQ_2/k_2)(\Delta F_{\omega_2,el}(x,y)+b(Q_2/k_c)\{[F_{\omega_2,el}(x_1,y_1)+\Delta F_{\omega_2,el}(x,y)]F_{el}'(x_2,y_2)-F_{\omega_2,el}(x_1,y_1)F_{el}'(x_1,y_1)\})$$

For large changes in surface potential ($\Delta\psi$ (x,y)) during scanning, will be dominated by the electrostatic force as is seen in the work of Stark and colleagues[7]. In contrast, for small changes in surface potential, such as those in the current experiments where $\Delta\psi$ (x,y) is very small (only the difference in potential between the mica substrate and the deposited protein and DNA molecules), $\Delta A_{\omega_2}$(x,y) will be dominated by the electrostatic force gradient. For these conditions, $\Delta A_{\omega_2}$(x,y)$\ll F_{\omega_2}$ and $$\Delta A_{\omega_2}(x,y) \approx (aQ_2/k_2)(\Delta F_{\omega_2,el}(x,y)+b(Q_2/k_c)F_{\omega_2,el}\Delta F_{el}'(x,y))$$

Because $F_{\omega_2,el}$ is sensitive to electrostatic potential over a greater distance than $F_{el}'$, the tip cone and the cantilever, as well as the tip apex, make contributions to $F_{\omega_2,el}$(x,y), and therefore, $F_{\omega_2,el}$(x,y) will be averaged over a greater area of the sample than $F_{el}'$(x,y)[4,9,11,13,24-26]. Consequently, for small changes in surface potential [$\Delta\psi \ll (\Delta\phi_{TS}-V_{DC})$] over an area similar to the tip radius, $F_{\omega_2,el}$(x,y) may be relatively constant. If the force is approximately constant as a function of position then $$\Delta A_{\omega_2}(x,y) \approx ab(Q_2^2/k_ck_2)F_{\omega_2,el}\Delta F_{el}'(x,y)$$

with only the force gradient contributing to $\Delta A_{\omega_2}$(x,y). (For the cantilevers used in our experimental setup, $k_c \approx 2.8$ N/m, $k_2 \approx 110$ Nm, $Q_1 \approx 170$, and $Q_2 \approx 500$.)

In our experiments, we take advantage of the fact that the mica is a negatively charged surface[6,27] and use $V_{DC}$ and a large $V_{AC}$ to generate an oscillation at $\omega_2$ and measure $\Delta A_{\omega_2}$ (x,y). Because [$\Delta\psi \ll (\Delta\phi_{TS}-V_{DC})$] for proteins and DNA deposited on mica[5,28], $\Delta A_{\omega_2}$(x,y) is dominated by $F_{el}'$. Furthermore, because we are operating in repulsive mode, if there is a significant force component to $\Delta A_{\omega_2}$(x,y), it will couple constructively with the force gradient component to increase the magnitude of $\Delta A_{\omega_2}$(x,y). Operating in repulsive mode also increases both the sensitivity and resolution by maintaining a constant minimum distance between the tip and the sample.

Conductive Cantilever Preparation

To obtain high-resolution topography and DREEM images, we used highly doped silicon cantilevers (PPP-FMR from Nanosensor; 2.8 N/m) instead of metal coated cantilevers, because the radius of curvature of the metal coated tip is $\sim 20$ nm, while that for the non-coated tip is $\sim 7$ nm. The conductivity of the doped cantilevers is comparable to that of the metal coated tips. It should be noted, however, that these doped silicon tips are easily oxidized, which results in the formation of a nanometer thin non-conductive oxidized layer. Consequently, to make a conductive connection between the cantilever and the external input power source, it is essential to penetrate the oxide layer. As described below, we have devised a straightforward method for making a reliable connection, by scraping the cantilever chip and simultaneously coating it with colloidal liquid silver. The silver on the chip makes contact with the metallic tip holder for the Asylum AFM system. For use with instruments that do not have grounded tip holders, ground wires can be attached with patch of liquid silver.

Detailed instructions for cantilever preparation. A small amount of the colloidal liquid silver (Ted Pella Inc. product #16034) is spread on a clean glass slide. The cantilever is held with one pair of tweezers. Another pair of tweezers is dipped in the liquid silver, and these silver coated tweezers are used to scrape and coat the edges of the silicon chip and the silicon surface of the chip on the side opposite from the cantilever tip. The scraping removes the oxidized silicon ($SiO_2$) layer on the surface and replaces it with a conductive silver layer. Once completed, the silver coated chip is allowed to dry for $\sim 5$ minutes. Once dry, it can be loaded into the AFM. This process simultaneously scratches away the oxide layer and covers the silicon with silver, preventing any oxidation and forming a conductive layer that can be easily connected to the external electrical sources.

Substrate Grounding

In our setup, the bias is applied to the tip and the sample is grounded. To ground the sample, which is deposited on mica, we use liquid silver to connect a thin piece of mica to a glass slide, and we also make a connection to ground using liquid silver. Specifically, after the sample has been deposited on mica, a box cutter is used to cleave a thin layer of mica containing the deposited samples (on the topside). The opposite side of the mica (the downside), which does not contain the sample, is coated with liquid silver and held in the air until the liquid silver is dried. This sample is then attached to a glass slide with liquid silver.

To prepare the glass slide, the center of a glass slide is coated with a patch of liquid silver at least as large as the mica. A streak of silver leading from this central patch to one of the furthest sides is painted, and the streak is continued for a short distance on the other side of the glass slide to ensure that it makes proper contact with the metal on the AFM base for grounding. The silver-coated mica is placed, silver side down, on the wet silver patch, and the slide is allowed to dry for $\sim 30$ minutes. It is important not to press down too hard when placing the mica on the silver patch to avoid causing patches where the there is no silver.

Selection of the Imaging Conditions

AFM topographic images are collected in standard repulsive intermittent contact mode at the fundamental resonance frequency ($\omega_1$) (MFP-3D AFM, Asylum Research). With the cantilevers used in this study (PPP-FMR from Nanosensor; 2.8 N/m), we found that the highest quality topographic images were obtained with a vibration amplitude of ~50 nm and a set point such that the force on the sample is minimized, while maintaining a repulsive interaction with surface. Not surprisingly, we found that the quality of the DREEM images is highly dependent on the quality of the topographic images.

To determine the optimum AC and DC biases for DREEM imaging, we measured $A_{\omega_2}$ and collected images as a function of $V_{AC}$ and $V_{DC}$ (from 0 to 20 V and −0.5 to 0.5 V, respectively) using the instrumental setup shown in FIG. 1a. When the tip is in contact with mica in either repulsive or attractive (noncontact) mode, $A_{\omega_2}$ increases linearly upon varying $V_{DC}$ from 0.5 to −0.3 V or $V_{AC}$ from 0 to 20 V (data not shown), as expected[6]. In general, we found that the DREEM image quality increases with increasing vibration amplitude at $\omega_2$. Notably, however, the largest amplitudes that we employed for DREEM imaging at the first overtone are very small (~1 nm) compared to the mechanical vibration (~50 nm) at the fundamental frequency, which prevents crosstalk of the electrical signal into the topographic signal. As expected, we also did not detect any crosstalk from the topography in the DREEM images. The time constant for collection of the DREEM signal at $\omega_2$ was 1 ms. Images were collected at a scan speed of 2 Hz, and the scan speed is limited by collection of the topographic signal, not the DREEM signal.

Sample Preparation, Deposition and Analysis

Prior to deposition, the mica was pealed to reveal a fresh surface and incubated in a desiccator with a 30 microliters of aminopropyl triethoxy silane (APTES) on a piece of parafilm for 15 minutes to modify the mica surface with a low density of amine groups to facilitate deposition of DNA[29]. The proteins and DNA were incubated together at room temperature for two minutes, crosslinked with 0.08% gluteraldehyde for 1 minute, and deposited on APTES-treated mica, rinsed with water and dried with nitrogen before imaging. Some protein-DNA complexes were purified using an approximately two-centimeter agarose bead gel filtration column prior to deposition to remove excess free proteins. The DNA is a linearized 2030 base pair plasmid containing a single GT-mismatch, which serves as a recognition site for MutS and MutSα, 375 base pairs from one end. The DNA lengths were measured using IGOR Pro. The volume analysis was done as described previously[18,30].

It will be understood that various details of the presently disclosed subject matter may be changed without departing from the scope of the presently disclosed subject matter. Furthermore, the foregoing description is for the purpose of illustration only, and not for the purpose of limitation.

REFERENCES

The disclosure of each of the following references is hereby incorporated herein by reference in its entirety.

1. Bazett-Jones, D. P. et al. *Nucleic Acids Res.* 24, 321-329, (1996).
2. Barth, C., Foster, A. S., Henry, C. R. & Shluger, A. L. *Adv. Mater.* 23, 477-501, (2011).
3. Nonnenmacher, M., O'Boyle, M. P. & Wickramasinghe, H. K. *Appl. Phys. Lett.* 58, 2921, (1991).
4. Glatzel, T. *Appl. Surf. Sci.* 210, 84-89, (2003).
5. Leung, C. et al. *Appl. Phys. Lett.* 97, 203703, (2010).
6. Mikamo-Satoh, E. et al. *Nanotechnology* 20, 145102, (2009).
7. Stark, R. W., Naujoks, N. & Stemmer, A. *Nanotechnology* 18, 065502, (2007).
8. Hoummady, M. & Farnault, E. *Appl. Phys. A* 66, 361-364, (1998).
9. Ding, X. D. et al. *Appl. Phys. Lett.* 94, 223109, (2009).
10. Albrecht, T. R., Grütter, P., Horne, D. & Rugar, D. *J. Appl. Phys.* 69, 668-673, (1991).
11. Martin, Y., Williams, C. C. & Wickramasinghe, H. K. *J. Appl. Phys.* 61, 4723-4729, (1987).
12. Cleveland, J., Anczykowski, B., Schmid, A. & Elings, V. *Appl. Phys. Lett.* 72, 2613, (1998).
13. Colchero, J., Gil, A. & Baró A. *Phys. Rev. B* 64, (2001).
14. Kunkel, T. A. & Erie, D. A. *Annu. Rev. Biochem.* 74, 681-710, (2005).
15. Obmolova, G., Ban, C., Hsieh, P. & Yang, W. *Nature* 407, 703-710, (2000).
16. Wang, H. et al. *Proc. Natl. Acad. Sci. USA* 100, 14822-14827, (2003).
17. Jiang, Y. & Marszalek, P. E. *EMBO J.* 30, 2881-2893, (2011).
18. Ratcliff, G. C. & Erie, D. A. *JACS* 123, 5632-5635, (2001).
19. Garcia, R. & Perez, R. *Surf. Sci. Rep.*, (2002).
20. Rast, S., Wattinger, C., Gysin, U. & Meyer, E. *Nanotechnology* 11, 169, (2000).
21. Takagi, A., Yamada, F., Matsumoto, T. & Kawai, T. *Nanotechnology* 20, 365501, (2009).
22. Hong, J. et al. *J. Vacuum Sci. Tech. B: Microelectronics and Nanometer Struct.* 16, 2942, (1998).
23. Hong, J., Park, S. & Khim, Z. *Rev. Sci. Instrum.* 70, 1735, (1999).
24. Giessibl, F. J. *Science* 267, 68-71, (1995).
25. Gil, A., Colchero, J., Gómez-Herrero, J. & Baró, A. *Nanotechnology* 14, 332, (2003).
26. Tevaarwerk, E. et al. *Rev. Sci. Instrum.* 76, 053707, (2005).
27. Naito, Y., Maeda, Y., Matsumoto, T. & Kawai, T. *Surf. Sci.* 459, L446-L450, (2000).
28. Leung, C. et al. *Nano Lett.* 9, 2769-2773, (2009).
29. Shlyakhtenko, L. S. et al. *Ultramicroscopy* 97, 279-287, (2003).
30. Yang, Y., Wang, H. & Erie, D. A. *Methods* 29, 175-187, (2003).

What is claimed is:

1. A method for performing enhanced electrostatic and atomic force microscopy, the method comprising:
    applying an alternating current (AC) bias and a direct current (DC) bias to an atomic force microscopy cantilever, wherein the AC bias has a frequency greater than a fundamental resonance frequency of the cantilever;
    mechanically vibrating the cantilever at a frequency different from the frequency of the AC bias and wherein applying the DC bias includes using the DC bias together with the AC bias to cause the cantilever to vibrate at the frequency greater than the fundamental resonance frequency of the cantilever;
    physically and electrostatically scanning a sample in the same pass using the cantilever while vibrating the cantilever and applying the AC and DC biases to the cantilever, and generating a topography image of the sample from the physical scanning and an electrostatic image of charged material under or on a surface of the sample from the electrostatic scanning, wherein physically and electrostatically scanning the sample includes monitoring a change in cantilever vibration amplitude as a function of sample position.

2. The method of claim 1 wherein the sample comprises a biological sample.

3. The method of claim 2 wherein the biological sample comprises a protein deoxyribonucleic acid (DNA) complex and wherein the electrostatic image includes an image of DNA under or on the surface of the protein DNA complex.

4. The method of claim 1 wherein the frequency of the AC bias substantially corresponds to the first overtone frequency of the cantilever.

5. The method of claim 1 wherein the frequency of the AC bias substantially corresponds to an overtone frequency of the cantilever greater than a first overtone frequency of the cantilever.

6. The method of claim 1 comprising monitoring an output signal produced by the scanning, wherein the output signal reflects changes in vibration of the cantilever induced by interaction between the AC bias and an electrostatic charge or surface potential of the sample.

7. The method of claim 6 comprising separating the output signal into a phase signal and an amplitude signal.

8. The method of claim 7 wherein the phase signal corresponds to local energy dissipation in the sample related to local polar properties of the sample due to dipole-dipole interactions, and the amplitude signal corresponds to electrical force and force gradient between the cantilever and the sample determined by surface charge density or surface potential of the sample.

9. The method of claim 1 comprising monitoring an overtone frequency of the cantilever and adjusting the DC bias applied to the cantilever or substrate to optimize an amplitude of vibration and frequency shift of the first overtone frequency, such that the vibration amplitude is sufficiently high and the AC bias substantially corresponds to the steepest shoulder of the overtone frequency of the cantilever after the cantilever is in contact with the surface of the sample.

10. The method of claim 1 wherein vibrating the cantilever includes mechanically vibrating the cantilever at a frequency substantially near a fundamental resonance frequency of the cantilever.

11. The method of claim 1 wherein the cantilever comprises a doped silicon material.

12. The method of claim 1 comprising grounding the sample by placing the sample on a thin atomically flat insulator attached to a conductive sample holder.

13. The method of claim 12 wherein the thin atomically flat insulator comprises freshly peeled mica.

14. The method of claim 1 comprising monitoring a frequency of the AC bias and/or adjusting the frequency of the AC bias such that the frequency of the AC bias substantially corresponds to an overtone frequency of the cantilever during scanning of the sample.

15. A system for performing enhanced electrostatic and atomic force microscopy, the system comprising:
applying an alternating current (AC) bias and a direct current (DC) bias to an atomic force microscopy cantilever, wherein the AC bias has a frequency greater than a fundamental resonance frequency of the cantilever;
mechanically vibrating the cantilever at a frequency different from the frequency of the AC bias and wherein applying the DC bias includes using the DC bias together with the AC bias to cause the cantilever to vibrate at the frequency greater than the fundamental frequency of the cantilever;
physically and electrostatically scanning a sample in the same pass using the cantilever while vibrating the cantilever and applying the AC and DC biases to the cantilever, and generating a topography image of the sample from the physical scanning and an electrostatic image of charged material under or on a surface of the sample from the electrostatic scanning, wherein physically and electrostatically scanning the sample includes monitoring a change in cantilever vibration amplitude as a function of sample position.

16. The system of claim 15 wherein the sample comprises a biological sample.

17. The system of claim 16 wherein the sample comprises a protein deoxyribonucleic acid (DNA) complex.

18. The system of claim 15 wherein the frequency of the AC bias substantially corresponds to a first overtone frequency of the cantilever.

19. The system of claim 15 wherein the frequency of the AC bias substantially corresponds to an overtone frequency of the cantilever greater than a first overtone frequency of the cantilever.

20. The system of claim 15 wherein the analysis module is configured to monitor an output signal produced by the scanning, wherein the output signal reflects changes in vibration of the cantilever induced by interaction between the AC bias and an electrostatic charge of the sample.

21. The system of claim 20 wherein the analysis module is configured to separate the output signal into a phase signal and an amplitude signal.

22. The system of claim 21 wherein the phase signal corresponds to local energy dissipation in the sample related to local polar properties of the sample due to dipole-dipole interaction, and the amplitude signal corresponds to electrical force and force gradient between the cantilever and the sample determined by surface charge density or surface potential of the sample.

23. The system of claim 15 wherein the function generator is configured to apply an adjustable AC bias to the cantilever and as well to the lock-in amplifier as a reference signal.

24. The system of claim 23 wherein the analysis module is configured to monitor an overtone frequency of the cantilever and adjust the DC bias to optimize an amplitude of vibration and a frequency shift of the first overtone frequency, such that the vibration amplitude is sufficiently high and the AC bias substantially corresponds to a steepest shoulder of the overtone frequency of the cantilever after the cantilever is in contact with the surface of the sample.

25. The system of claim 15 wherein the atomic force microscope is configured to mechanically vibrate the cantilever substantially near a fundamental resonance frequency of the cantilever.

26. The system of claim 15 wherein the cantilever comprises a doped silicon material.

27. The system of claim 15 wherein the sample is grounded by placing the sample on a thin atomically flat insulator with a thickness around 50 micro meters attached to a conductive sample holder.

28. The system of claim 27 wherein the thin atomically flat insulator comprises freshly peeled mica.

29. The system of claim 15 wherein the analysis module is configured to monitor a frequency of the AC bias and/or adjust the frequency of the AC bias such that the frequency of the AC bias substantially corresponds to an overtone frequency of the cantilever during scanning of the sample.

30. A non-transitory computer readable medium comprising computer executable instructions that when executed by a processor of a computer control the computer to perform steps comprising:
applying an alternating current (AC) bias and a direct current (DC) bias to an atomic force microscopy cantilever, wherein the AC bias has a frequency greater than a fundamental resonance frequency of the cantilever;

mechanically vibrating the cantilever at a frequency different from the frequency of the AC bias and wherein applying the DC bias includes using the DC bias together with the AC bias to cause the cantilever to vibrate at the frequency greater than the fundamental resonance frequency of the cantilever;

physically and electrostatically scanning a sample in the same pass using the cantilever while vibrating the cantilever and applying the AC and DC biases to the cantilever, and generating a topography image of the sample from the physical scanning and an electrostatic image of charged material under or on a surface of the sample from the electrostatic scanning, wherein physically and electrostatically scanning the sample includes monitoring a change in cantilever vibration amplitude as a function of sample position.

* * * * *